(12) United States Patent
Kogan

(10) Patent No.: US 7,542,547 B2
(45) Date of Patent: Jun. 2, 2009

(54) X-RAY DIFFRACTION EQUIPMENT FOR X-RAY SCATTERING

(75) Inventor: Vladimir Kogan, Euschede (NL)

(73) Assignee: PANalytical B.V., Almelo (NL)

( * ) Notice: Subject to any disclaimer, the term of this patent is extended or adjusted under 35 U.S.C. 154(b) by 0 days.

(21) Appl. No.: 12/014,437

(22) Filed: Jan. 15, 2008

(65) Prior Publication Data

US 2008/0175352 A1    Jul. 24, 2008

(30) Foreign Application Priority Data

Jan. 19, 2007    (EP) .................................. 07100858

(51) Int. Cl.
*G01N 23/20* (2006.01)
(52) U.S. Cl. .......................................... 378/81; 378/71
(58) Field of Classification Search ............. 378/70–90, 378/145
See application file for complete search history.

(56) References Cited

U.S. PATENT DOCUMENTS 4,263,510 A * 4/1981 Ciccarelli et al. ............. 378/46

2004/0028179 A1    2/2004  Rosso et al. ................... 378/70

FOREIGN PATENT DOCUMENTS

WO    WO 00/23795    4/2000
WO    WO 01/44793    6/2001

OTHER PUBLICATIONS

European Patent Office, European Search Report—Application No. EP 07 10 0858, dated Aug. 16, 2007, 5 pages.
Ladell, J. et al., "*Cu $Ka_2$ Elimination Algorithm*," J. Appl. Cryst. 8, 499-506 (1975).

* cited by examiner

*Primary Examiner*—Courtney Thomas
(74) *Attorney, Agent, or Firm*—Bromberg & Sunstein LLP

(57) ABSTRACT

An X-ray scattering chamber 12 includes a housing 14 that may be mounted in X-ray diffraction equipment between an X-ray source 2 and an X-ray detector 4, for example on goniometer arm 6. The housing 14 includes sample holder 16 and beam conditioning optics 22,24, but the system also makes use of primary optics 10 outside the housing. The equipment is suitable for SAXS and/or SAXS-WAXS.

12 Claims, 2 Drawing Sheets

X-RAY DIFFRACTION EQUIPMENT FOR X-RAY SCATTERING

CROSS REFERENCE TO RELATED APPLICATIONS

This application claims priority from European Patent Application Serial No. EP 07100858.5, filed on Jan. 19, 2007, which is hereby incorporated by reference, in its entirety.

TECHNICAL FIELD

The invention relates to equipment for carrying out X-ray scattering experiments, including in particular wide-angle X-ray scattering (WAXS) and small-angle X-ray scattering (SAXS).

BACKGROUND ART

X-ray diffraction is a well known technique in which an X-ray beam is directed at a sample and the diffracted, or scattered, X-rays are measured to obtain information about the sample. The diffraction angle is related to the length scale probed by the measurements—larger length scales correspond to smaller scattering angles.

Small angle X-ray scattering is a measurement technique that is used for structural investigation in the nm range. An X-ray beam is directed at a sample, and the intensity as a function of scattering angles is measured for small scattering angles, typically less than 7°. At these small angles, the X-ray beam can probe structure in the sample at a slightly larger length scale than the sub-nm range probed by conventional, wide angle X-ray diffraction.

Unlike conventional X-ray diffraction (XRD) techniques, the sample for small angle scattering need not be crystalline, and so the technique may be used for determining properties of macromolecules and partially ordered structures for which X-ray diffraction is not suitable. The sample need not be in solid form and the technique can be used on liquids, solutions and suspensions, as well as solids.

Most applications of SAXS require vacuum isolation to prevent air scattering.

Typically, SAXS equipment consists of a vacuum housing, which is fixed to a separate X-ray source. The housing contains a sample holding portion, various X-ray alignment components including in particular some beam conditioners to restrict the incident beam trajectories and a beam stop to absorb X-rays that are not scattered at all. X-ray detector may be based inside or outside the housing.

The SAXS technique is not as widely used as might be expected, but this may well be due to the required dedicated equipment. The use of conventional XRD equipment to detect small angle scattered radiation has not given the best quality results Wide angle X-ray scattering (WAXS) is a similar approach at larger angles. WAXS may target the scattering from periodic patterns of electron density or the scattering from isolated particles, measurements complimentary to SAXS.

SUMMARY OF INVENTION

According to a first aspect of the invention, there is provided an X-ray diffractometer that includes an X-ray source for directing incident x-rays to a sample measurement position, and an X-ray detector for detecting output x-rays from the sample measurement position. A goniometer adjusts the position of at least one of the source, detector and the sample.

A detachable x-ray scattering chamber includes a gas-tight housing having an x-ray input window for receiving incident x-rays from the x-ray source and an x-ray output window for passing the scattered x-rays to the x-ray detector. The chamber further includes at least one beam conditioner between the x-ray input window and sample measurement position for conditioning the incident beam and at least a beam stop between the sample measurement position and the x-ray output window; and a mounting means for detachably mounting the chamber in position.

In accordance with another embodiment of the invention, there is provided an X-ray scattering chamber adapted to be mounted in an X-ray diffractometer including an X-ray source, an X-ray detector, and a goniometer for adjusting the position of at least one of the source and detector around the sample measurement position. The X-ray scattering chamber includes a mount for reproducible placement and removal of the chamber. The X-ray scattering chamber further includes: a gas-tight housing having an x-ray input window for receiving x-rays from the x-ray source and an x-ray output window for passing the scattered output x-rays to the x-ray detector; and at least one beam conditioner between the x-ray input window and sample measurement position for conditioning the incident beam and at least one beam stop between the sample measurement position and the x-ray output window for conditioning the output x-rays. The X-ray scattering chamber may also include a sample holder in the form of a flow-through tube.

In illustrative embodiments, the invention uses a detachable chamber isolated from atmosphere in a conventional diffractometer. The chamber may be easily introduced or removed by a single mount.

The chamber allows measurements to be made in a conventional diffractometer but ensures that a substantial part of the X-ray beam path is through x-ray scattering chamber which is isolated from atmosphere. This allows the beam to pass through a vacuum or a selected gas as required. For some applications this improves the measurements compared with conventional diffractometry in which the interactions of X-rays with air can be the source of intense background scattering.

A further benefit of the approach is that some elements such as beam conditioners may be provided in the detachable x-ray scattering chamber both before and after the sample, that is to say on both primary and secondary sides. The beam conditioners can be fixed in and aligned in the detachable x-ray scattering chamber once. The chamber is simply and quickly fixed into place in conventional equipment, and can be removed as quickly when no longer required. This speeds up measurements and increases flexibility.

By providing the chamber to be fitted into conventional X-ray diffractometer—in particular the conventional type with a goniometer—there is no need for users of the equipment to obtain dedicated system equipped with the camera to conduct experiments with the vacuum/gas isolation of beampath.

The approach is particularly suitable for making SAXS measurements. The invention allows high quality SAXS measurements to be made without requiring a complete bespoke SAXS system.

The beam conditioners may include a beam stop mounted between the small angle scattering sample holder and the X-ray outlet window for stopping unscattered X-rays. By including the beam stop in the vacuum housing problems that may arise when X-rays are scattered off the beam stop into air and hence cause emissions from the air are avoided.

The beam conditioning optics may also include a primary beam conditioners between the X-ray input window and the small angle scattering sample holder. By mounting the primary beam conditioners in the same housing as the beam stop the perfect labirint is created preventing strong direct beam components from influencing useful scattered intensity. Thus, by placing the chamber into conventional XRD equipment the optimal configuration for conducting SAXS measurement is obtained without excessive adjustment.

The invention may also allow for WAXS measurements. In this case, the X-ray scattering chamber may be shaped to provide a path for X-rays scattered by a sample in the small angle scattering sample holder by an angle up to a predetermined angle, where the predetermined angle is in the range 10° to 90°.

There are some also applications of conventional X-Ray diffraction where it is beneficial to have the sample and significant part of the X-ray trajectories in vacuum or in the nonambient atmosphere, and the invention may also have particular benefit for these.

The diffractometer may include primary optics between the X-ray source and X-ray diffractometer chamber.

The primary optics may include a monochromator, an elliptic or parabolic x-ray mirror or a hybrid type optic.

BRIEF DESCRIPTION OF DRAWINGS

For a better understanding of the invention, embodiments will now be described purely by way of example, with reference to the accompanying drawings, in which.

Like or corresponding components are given the same reference numerals in the different figures, which are schematic and not to scale.

DETAILED DESCRIPTION

Figure 1:
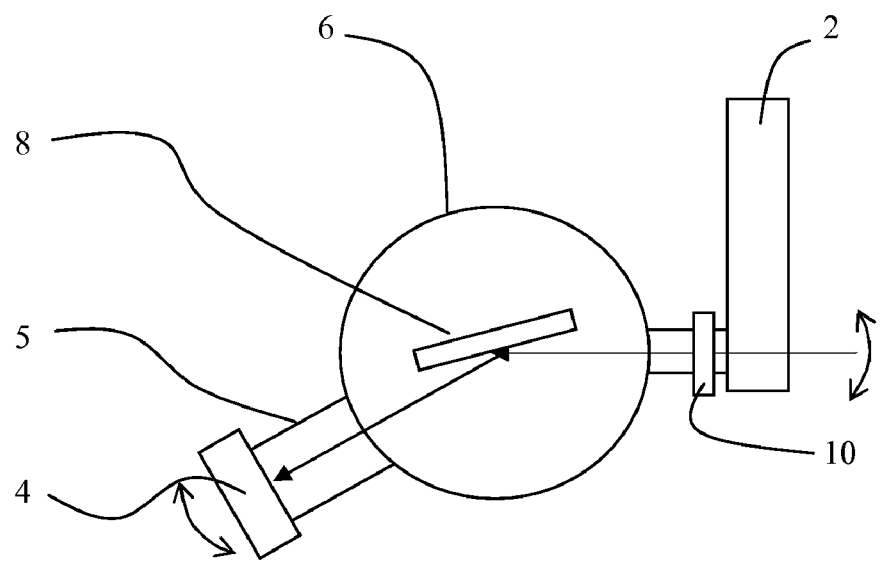
FIG. 1 shows an X-ray diffractometer according to the invention without the scattering chamber mounted.

Referring to FIG. 1, the X-ray diffractometer according to the first embodiment includes X-ray source 2 and X-ray detector 4. A pair of goniometer axes 6 are provided and the source 2 and detector 4 are each mounted on a goniometer axes 6. If required, the source and detector are mounted on the goniometer by means of arms 5. A first sample holder 8 is arranged for mounting an x-ray sample at a measurement position. Both the X-ray source 2 and the X-ray detector 4 can be rotated about the measurement position. X-ray primary optics 10, for example a collimator and/or a monochromator, are provided between the X-ray source and the sample stage.

Alternatively, the source 2 may be fixed, the sample holder 8 may rotate on one goniometer axis 6 and the detector 4 on another goniometer axis 6. Other configurations are possible as will be appreciated by those skilled in the art.

In use as a conventional X-ray diffractometer, a sample is mounted on the first diffraction sample holder 8 and the X-ray diffraction (XRD) sample holder 8 and X-ray detector 4 are rotated to carry out an X-ray diffraction scan.

Figure 2:
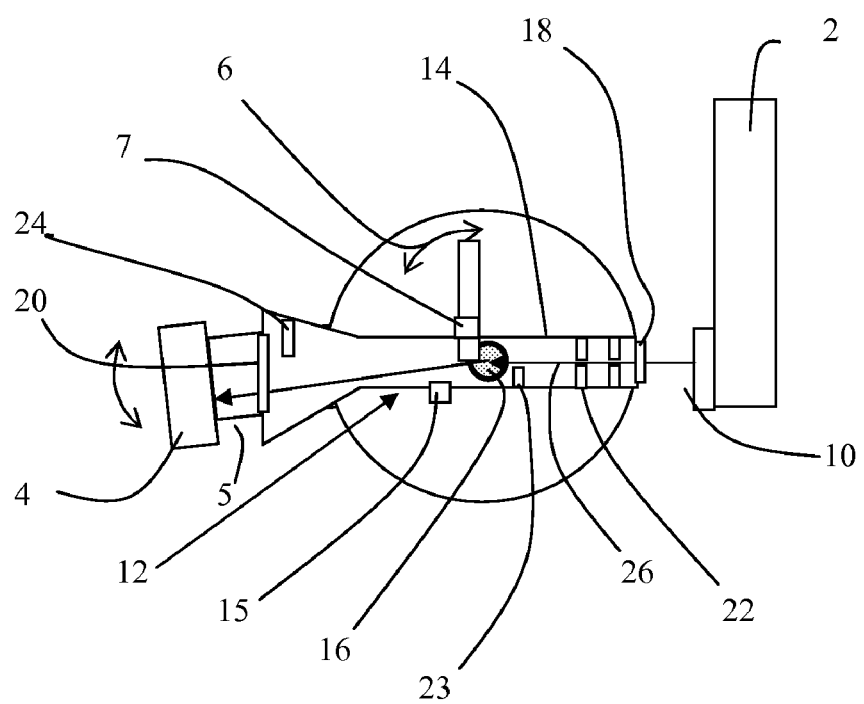
FIG. 2 shows the X-ray diffractometer of FIG. 1 with the chamber mounted.

As illustrated in FIG. 2, the system may also be used to carry out small angle X-ray scattering. The first XRD sample holder 8 is simply removed from the beam path. Alternatively, the XRD sample holder 8 may be shifted out of the beam path.

In place of the XRD sample holder 8 is detachably mounted an x-ray scattering chamber 12. The x-ray scattering chamber 12 is detachably mounted on the goniometer axis 6 by mounting means 7. The means may be include a mounting plate and screws, an arm, or any suitable fixing technique. The x-ray scattering chamber 12 can be mounted in the system for carrying out measurements and removed again to allow the system to once again carry out conventional measurements. The x-ray scattering chamber 12 is mounted reproducibly, i.e. when it is replaced the x-ray scattering chamber 12 is closely aligned to its previous position.

The chamber 12 includes a gas-tight housing 14 (also known in embodiments as a tube) and a second sample holder 16. A port 15 allows the housing 14 to be evacuated as the housing is vacuum tight. Alternatively, if required, the housing can be filled with gas.

The chamber 12 also includes an inlet window 18 and an outlet window 20. Beam conditioners 22, 23 are mounted between the inlet window 18 and the second sample holder 16 and a beam stop 24 is mounted between the second sample holder 16 and the outlet window. The beam stop 24 may be considered as a secondary beam conditioner.

The beam conditioners in particular include primary beam conditioners 22,23 between the inlet window and the sample holder 16. These include a plurality of slits 22 along the beam path, and then a last primary beam conditioner 23. X-rays not passing through the slits 22 are substantially attenuated. Slits are preferred instead of parallel plate collimators since parallel plate collimators can cause scattering, though parallel plate collimators may alternatively or additionally be used if required.

The last primary beam conditioner 23 is arranged adjacent to the second sample holder 16 and is intended to remove all parasitic scattering from the other primary conditioners. Beam stop 24 is provided between the sample holder 16 and the outlet window 20. The primary beam conditioners 22,23 and beam stop 24 cooperate to stop un-scattered X-rays reaching the outlet window 20. Note that the last primary beam conditioner 23 and beam stop 24 are arranged on opposite sides of the X-ray beam path 26.

Although the term "beam stop" is used the beam stop does not completely stop the beam but merely substantially attenuates the unscattered beam by at least a factor $10^4$.

In use, X-rays are input along an X-ray beam path 26 from the X-ray source 2 through X-ray input window 18, pass through the primary beam conditioners 22,23 and hit the sample in the sample holder 16. X-rays that are not scattered by the sample proceed to the beam stop 24 where they are absorbed. Scattered X-rays pass the beam stop 24 and pass through outlet window 20 where they are detected by detector 4. The detector may be moved about a goniometer axis 6 on arm 5 if required. Alternatively, the detector may be a detector array capable of measuring X-rays over a range of angles in parallel; in this case, movement of the detector may not be required.

The embodiment delivers a number of advantages.

In this embodiment, the chamber 12 is a SAXS chamber. In conventional SAXS equipment reliability is assured by mounting all components apart from the X-ray source in a single housing designed specifically for SAXS measurements. The inventor has realised that in fact the key components are the primary beam conditioners, beam stop and sample holder and that these can be integrated into a single detachable housing. In this way, some expensive parts of an X-ray system such as the source, detector, generator and X-ray shielding can be reused in the conventional XRD equipment.

Previous attempts to carry out SAXS on conventional equipment have not used vacuum and have not mounted the primary beam conditioners, beam stop and sample holder on a single chassis. Results obtained with such systems are limited—the lack of vacuum and absence of traditional SAXS arrangement of beam conditioners significantly reduces sensitivity for SAXS applications.

Using the embodiment, unlike conventional SAXS equipment, the SAXS chamber does not include its own detector, and the SAXS chamber may be used with conventional XRD equipment. Thus, the additional cost of SAXS is greatly reduced compared with prior solutions.

In the embodiment using the chamber 12 in combination with conventional XRD equipment, the results of SAXS measurements are good because the SAXS chamber both provides the vacuum necessary for best quality results and also ensures precise alignment between primary beam conditioners 22,23 SAXS sample holder 16 and beam stop 24. Thus, the quality of results is much better than obtained simply measuring small angle scattering in conventional XRD equipment in which the X-rays pass through air and in which the arrangement used in the embodiment for SAXS measurements is impossible.

In particular, the provision of the primary conditioners 22 and beam stop 24 within the vacuum chamber avoids scattered X-rays interacting with air and hence causing further emissions which would otherwise reach detector 4 and worsen the quality of results.

By fixing the primary beam conditioners 22 in the same housing as the sample holder 16 the primary beam conditioners may in essence be pre-aligned. This means that the SAXS chamber 12 may be simply mounted in place without the need for excessive alignment procedures.

A further benefit of the specific embodiment is that the SAXS chamber 12 is mounted to be accurately aligned when attached without requiring further alignment. Hence, the SAXS chamber is able to cope with a variety of primary optics near the x-ray source and is accurately aligned with the X-ray source 2.

In alternative embodiments the SAXS chamber 12 could simply be mounted inside the XRD equipment not to the goniometer axis 6 but instead to the base of the cabinet or elsewhere.

Further improvements are possible. The primary optics 10 may include an elliptical mirror. The use of an elliptical mirror in SAXS is known and will accordingly not be described further here.

A further alternative is to use a so-called hybrid monochromator as the primary optics 10. In this case, the primary optics include a combination of a parabolic mirror and a crystal.

Returning to the complete system, various components may be quickly and easily removed and exchanged. It is particularly advantageous to provide click-on exchange of various components, so that they can be quickly and easily exchanged. This applies to the different primary optics, different X-ray tubes, and different detectors.

Indeed, it is possible to use two dimensional detectors or multiple detectors as well as more conventional detectors which measure X-ray intensity as a function of angle in a single direction only.

The sample holder 16 preferably holds a tube, for example a capillary. The tube may be sealed in place with o-rings to maintain the vacuum integrity of the vacuum housing 14.

The sample holder 16 may include the possibility to vary the temperature of the sample.

Figure 3:
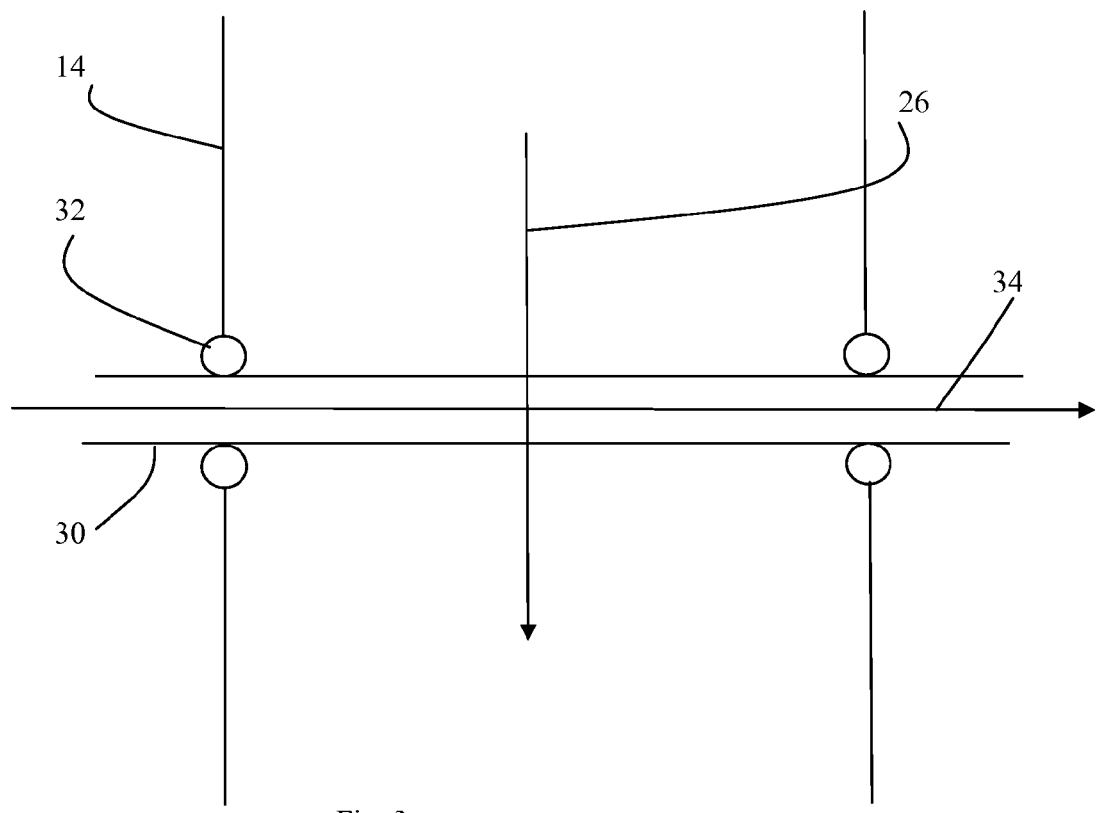
FIG. 3 illustrates a further embodiment with a flow-through sample holder.

As an alternative, a flow-through type sample holder may be used as illustrated in FIG. 3. The tube 30 passes through the housing 14 and is sealed, as illustrated schematically by o-rings 32. In this case, liquid 34 may flow through the sample holder during measurement and is measured by X-rays travelling along beam path 26.

Such an arrangement may also be used for powders.

The x-ray scattering chamber 12 may optionally allow for a bespoke detector to be integrated within the x-ray scattering chamber 12, either inside the housing 14 or outside.

In use, some applications may use a specific gas in the x-ray scattering chamber 12 instead of a vacuum. The gas-tight housing allows this option also.

Note that the chamber sample holder 16 need not be integrally formed with the chamber 12. In some embodiments, the sample holder may connect to the ambient outside the gas-tight sample chamber—this allows the x-ray beam pass to be in one atmosphere, or through a vacuum, while exposing the sample to a different atmosphere. The sample may be removed and replaced with the chamber 12 remaining fixed. In other embodiments, the sample holder 16 is within the chamber 12 and is removed and replaced together with chamber 12.

A further development is to include some of the functions provided in the above embodiment by the primary optics 10 integrally with the chamber 12 preferably inside but also possibly fixed to the outside of the housing 14. For example, a monochomator may be provided inside the tube, which may be a elliptical monochromator or a hybrid monochromator.

In the arrangement of FIG. 2, the SAXS chamber is mounted essentially horizontally and the X-ray path is essentially horizontal. However, this is not essential and it is possible to mount the SAXS chamber vertically in suitable equipment.

Figure 4:
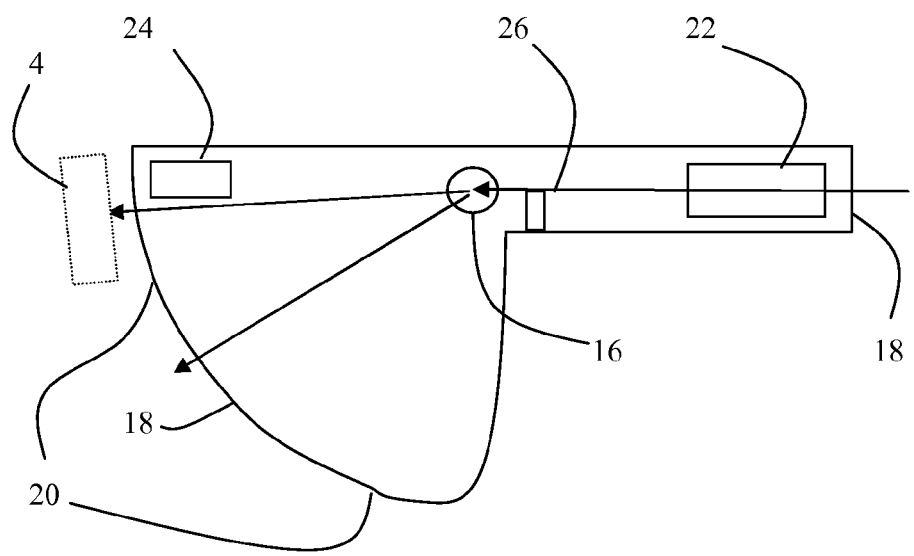
FIG. 4 shows a chamber according to a yet further embodiment.

Although the embodiment described above uses the chamber for SAXS, other chambers may be used for other types of measurement In a further embodiment, the SAXS chamber is of a different shape illustrated in FIG. 4 so that both small and large angle scattering can be measured, using a so-called SAXS-WAXS technique. The outlet window 18 is much larger than in the embodiment of FIG. 2. In this case the maximum scattering angle may be 90°. The detector 4 may be moved to various positions to capture both small angle and wide angle scattering data.

Alternative embodiments are not specially adapted to SAXS at all but merely use the chamber to mount the beam conditioning optics before and after the measurement position and to ensure the beam path is through vacuum or chosen gas. This improves measurement quality by avoiding X-rays scattered by the collimator or beam stops from interacting with air and creating additional spurious X-rays reaching the detector.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

What is claimed is:

1. An X-ray diffractometer, comprising:
    an X-ray source for directing incident x-rays to a sample measurement position;

an X-ray detector for detecting output x-rays from the sample measurement position;

a goniometer for adjusting the position of at least one of the source, detector and the sample; and an detachable x-ray scattering chamber including:

a gas-tight housing having an x-ray input window for receiving incident x-rays from the x-ray source and an x-ray output window for passing the scattered x-rays to the x-ray detector;

at least one beam conditioner between the x-ray input window and sample measurement position for conditioning the incident beam and at least a beam stop between the sample measurement position and the x-ray output window; and mounting means for detachably mounting the chamber in position.

2. An X-ray diffractometer according to claim 1 comprising a plurality of exchangeable sample holders, including a first sample holder for holding a sample at the sample measurement position with the x-ray scattering chamber detached; and a second sample holder attached to the x-ray scattering chamber for holding a sample in the x-ray scattering chamber at the sample measurement position with the x-ray scattering chamber attached.

3. An X-ray diffractometer according to claim 1 wherein the detector is mounted on the goniometer.

4. An X-ray diffractometer according to claim 1 wherein beam-conditioners in the x-ray scattering chamber between the input window and the sample measurement position includes at least one slit.

5. An X-ray diffractometer according to claim 1 wherein the X-ray scattering chamber is shaped to provide a path for X-rays scattered by a sample in the measurement position by an angle up to a predetermined angle, where the predetermined angle is in the range 10° to 140°.

6. An X-ray diffractometer according to claim 1 further comprising primary beam optics between the X-ray source and the X-ray scattering chamber.

7. An X-ray diffractometer according to claim 6 wherein the primary beam optics includes an x-ray mirror and/or a crystal monochromator.

8. An X-ray scattering chamber, adapted to be mounted in an X-ray diffractometer including an X-ray source, an X-ray detector, and a goniometer for adjusting the position of at least one of the source and detector around the sample measurement position, the X-ray scattering chamber comprising:

a mount for reproducible placement and removal of the chamber;

a gas-tight housing having an x-ray input window for receiving x-rays from the x-ray source and an x-ray output window for passing the scattered output x-rays to the x-ray detector; and at least one beam conditioner between the x-ray input window and sample measurement position for conditioning the incident beam and at least one beam stop between the sample measurement position and the x-ray output window for conditioning the output x-rays.

9. An X-ray scattering chamber according to claim 8 for carrying out measurements wherein the beam conditioner is adapted to cooperate with the beam stop to stop x-rays not scattered by a sample at the sample measurement position from reaching the detector.

10. An X-ray scattering chamber according to claim 8 wherein the X-ray scattering chamber is shaped to provide a path for X-rays scattered by a sample in the measurement position by an angle up to a predetermined angle, where the predetermined angle is in the range 10° to 140°.

11. An X-ray scattering chamber according to claim 8 further comprising a sample holder in the form of a flow-through tube.

12. A method of operation of an X-ray scattering chamber having a mount for reproducible placement and removal of the chamber;

a gas-tight housing having an x-ray input window for receiving x-rays from the x-ray source and an x-ray output window for passing the scattered output x-rays to the x-ray detector; and at least one beam conditioner between the x-ray input window and sample measurement position for conditioning the incident beam and at least one beam stop between the sample measurement position and the x-ray output window for conditioning the output x-rays;

including:

detachably mounting the X-ray scattering chamber in the X-ray diffraction equipment;

carrying out measurements on a sample with the x-ray scattering camera attached detaching the X-ray scattering chamber from the X-ray diffraction equipment.

* * * * *

UNITED STATES PATENT AND TRADEMARK OFFICE
CERTIFICATE OF CORRECTION

PATENT NO.         : 7,542,547 B2                                        Page 1 of 1
APPLICATION NO. : 12/014437
DATED              : June 2, 2009
INVENTOR(S)        : Kogan It is certified that error appears in the above-identified patent and that said Letters Patent is hereby corrected as shown below:

In Col. 7, line 5
replace "an detachable"
with "a detachable"

Signed and Sealed this

Twentieth Day of October, 2009

David J. Kappos
*Director of the United States Patent and Trademark Office*